(12) United States Patent
Thompson et al.

(10) Patent No.: US 9,519,844 B1
(45) Date of Patent: Dec. 13, 2016

(54) INFRARED THERMOGRAPHIC METHODS FOR WRINKLE CHARACTERIZATION IN COMPOSITE STRUCTURES

(71) Applicant: The Boeing Company, Chicago, IL (US)

(72) Inventors: Jeffrey G. Thompson, Auburn, WA (US); Gary E. Georgeson, Tacoma, WA (US); Tyler M. Holmes, Seattle, WA (US); Hong Hue Tat, Redmond, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/004,119

(22) Filed: Jan. 22, 2016

(51) Int. Cl.

| | |
|---|---|
| *G01J 5/00* | (2006.01) |
| *G06K 9/62* | (2006.01) |
| *H04N 7/18* | (2006.01) |
| *H04N 5/33* | (2006.01) |
| *H04N 5/225* | (2006.01) |
| *G06T 7/00* | (2006.01) |
| *G01J 5/02* | (2006.01) |
| *G01N 25/72* | (2006.01) |

(52) U.S. Cl.
CPC ............ *G06K 9/6267* (2013.01); *G01J 5/02* (2013.01); *G01N 25/72* (2013.01); *G06K 9/6215* (2013.01); *G06T 7/004* (2013.01); *G06T 7/0051* (2013.01); *H04N 5/2256* (2013.01); *H04N 5/33* (2013.01); *H04N 7/18* (2013.01); *G06T 2207/30248* (2013.01)

(58) Field of Classification Search
CPC ............... G01J 5/02; G01J 5/08; G01J 5/02; G01N 25/72

USPC ................... 250/338.1, 341.6, 347
See application file for complete search history.

(56) References Cited

U.S. PATENT DOCUMENTS

| | | | |
|---|---|---|---|
| 6,751,342 B2 * | 6/2004 | Shepard | G01N 25/72 250/332 |
| 7,075,084 B2 | 7/2006 | Thompson et al. | |
| 7,119,338 B2 | 10/2006 | Thompson et al. | |

(Continued)

OTHER PUBLICATIONS

U.S. Appl. No. 14/614,198, Safai et al., filed Feb. 4, 2015.

*Primary Examiner* — David Porta
*Assistant Examiner* — Meenakshi Sahu
(74) *Attorney, Agent, or Firm* — Ostrager Chong Flaherty & Broitman P.C.

(57) ABSTRACT

Methods for identifying and quantifying wrinkles in a composite structure by processing infrared imaging data. Temperature versus time profiles for all pixels in the field of view of an infrared camera are calculated, enabling thermal signatures to be produced. By comparing the thermal signature of the part under test with the thermal signature of a reference standard representing a similar part having wrinkles of known size and shape, the presence of wrinkles can be detected. The wrinkle wavelength can be determined by measuring the infrared image and applying a transfer function. If the geometric information acquired using infrared thermography does not reach a certain quality factor (for a quality prediction) or is incomplete, an ultrasonic transducer array probe running wrinkle quantification software can be rotated into position and scanned over the wrinkle area. The ultrasonic imaging data can be combined with the infrared imaging data to enable an improved quantification of the wrinkle geometry.

20 Claims, 12 Drawing Sheets

(56) References Cited

U.S. PATENT DOCUMENTS

| | | | |
|---|---|---|---|
| 7,186,981 B2 | 3/2007 | Shepard et al. | |
| 7,287,902 B2 | 10/2007 | Safai et al. | |
| 7,699,521 B2 | 4/2010 | Shepard | |
| 7,724,925 B2 * | 5/2010 | Shepard | G01N 25/72 |
| | | | 382/115 |
| 8,338,787 B1 | 12/2012 | Shelley, Jr. et al. | |
| 8,449,176 B2 | 5/2013 | Shepard | |
| 8,499,632 B1 | 8/2013 | Ihn et al. | |
| 8,853,634 B2 | 10/2014 | Shelley, Jr. et al. | |
| 8,981,771 B2 | 3/2015 | Thompson | |
| 2012/0219034 A1 | 8/2012 | Nielsen | |
| 2015/0161778 A1 * | 6/2015 | Henderkott | G06T 7/0008 |
| | | | 348/129 |

\* cited by examiner

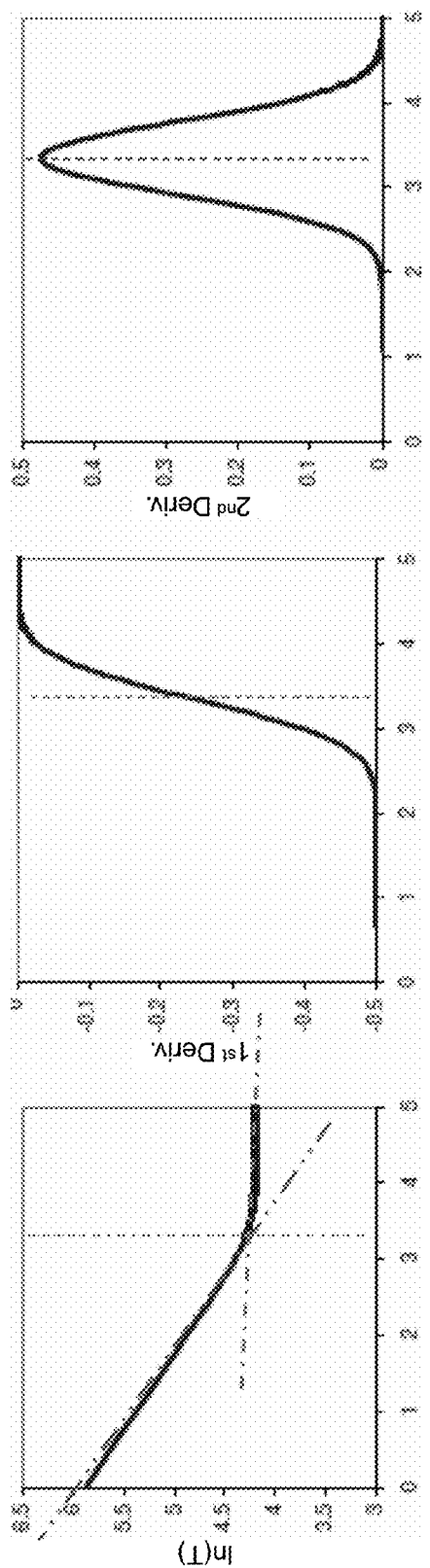

INFRARED THERMOGRAPHIC METHODS FOR WRINKLE CHARACTERIZATION IN COMPOSITE STRUCTURES

BACKGROUND

This disclosure generally relates to non-destructive inspection of structures or parts, and more particularly to systems and methods for characterizing or evaluating anomalies, such as wrinkles, in a laminate structure, such as a composite structure or similar structure.

New, lightweight composite materials and designs are being used more extensively in the aerospace industry for commercial aircraft and other aerospace vehicles, as well as in other industries. The structures using these composite materials may be formed using multiple plies or layers of fiber-reinforced plastic material that may be laminated together to form a lightweight, high-strength structure. Fabrication of composite laminate structure for aerospace applications can result in unwanted out-of-plane wrinkling of plies that can impact performance of the structure based on the size of the wrinkle. Quality assurance and certification for production parts in industries such as the aircraft industry requires that the part be built to meet certain design standards and specifications. For some parts there may be a standard acceptance criteria based on wrinkle size. Accordingly being able to accurately detect and measure the size of any wrinkles in a structure or part is desirable.

Some wrinkles can be identified visually from the surface. However, they cannot be quantified visually, so in an abundance of caution the worst case may be assumed unless means for measuring the size of the wrinkle (often in terms of length L divided by height D) can be provided. Also, wrinkles deeper in the structure cannot be seen visually from the surface at all. Ultrasonic methods have been developed to identify and quantify wrinkles. However, the main drawback of ultrasonic methods is that they cannot "see" beneath a wrinkle (and no access is available to the back side of the structure), so the amount of "good" material is unknown. Therefore, the maximum thickness of a wrinkle from its highest peak to the back surface may have to be assumed. This may result in overly conservative knockdowns of strength predictions, and needless and costly repairs. Another drawback of the ultrasonic method in general is that it takes significant time to collect the data. If a means were available to speed up the process through another inspection method—and still identify and/or quantify the size of wrinkles—that would be advantageous. In particular, processes for fabricating fuselages and fuselage sections could benefit from a wide-area method to detect and quantify wrinkles.

SUMMARY

The subject matter disclosed herein is directed to methods for identifying and quantifying wrinkles in a composite structure by processing infrared imaging data. Temperature versus time profiles for all pixels in the field of view of an infrared camera are calculated, enabling thermal signatures to be produced. By comparing the thermal signature of the part under test with the thermal signature of a reference standard representing a similar part having wrinkles of known size and shape, the presence of wrinkles can be detected. The wrinkle wavelength can be determined by measuring the infrared image and applying a transfer function. If the geometric information acquired using infrared thermography does not reach a certain quality factor (for a quality prediction) or is incomplete, an ultrasonic transducer array probe running wrinkle quantification software can be rotated into position and scanned over the wrinkle area. The ultrasonic imaging data can be combined with the infrared imaging data to enable an improved quantification of the wrinkle geometry.

The infrared imaging data captured by the infrared cameras can be processed to detect internal defects, particularly wrinkles, in composite structures. A computer system can be programmed to locate and quantify those types of anomalies based on at least the infrared imaging data. The system can collect inspection data for detecting wrinkles over large surface areas of the composite structure very rapidly and also quantifying a dimensional parameter of the wrinkles identified.

The systems and methods disclosed in detail below apply flash thermography equipment and software in defined ways to identify and measure wrinkles. The infrared camera records the surface temperature as an applied heat pulse diffuses into the surface of the part. The image acquisition time is adjusted to match the thickness and thermal properties of the material under test. Temperature versus time profiles for all pixels in the field of view are calculated, enabling thermal signatures to be produced. By comparing the thermal signature of the part with the thermal signature of a reference representing a similar part having wrinkles of known size and shape, the presence of wrinkles can be detected. For example, the thermal signature may be based on a logarithmic first derivative of temperature versus time (i.e., $d[\ln(T)]/d[\ln(t)]$). In accordance with some embodiments, the thermal images are enhanced by viewing an image created by intensities related to the second derivative (i.e., $d^2[\ln(T)]/d^2[\ln(t)]$) and applying a high pass filter to the image.

The wrinkle wavelength can be determined by measuring the infrared image and applying a correction factor (referred to hereinafter as a "transfer function"). If the geometric information acquired using infrared thermography does not reach a certain quality factor (for a quality prediction) or is incomplete, an ultrasonic transducer array probe running wrinkle quantification software can be rotated into position and scanned over the wrinkle area. The ultrasonic imaging data can be combined with the infrared imaging data to enable an improved quantification of the wrinkle geometry. (The infrared imaging data may provide information about the amount of good material under a wrinkle that the ultrasonic imaging data cannot provide.) That information can be sent, along with orientation information, to a plug-in for a finite element-based stress model using structural codes or to a stress analyst to determine the impact of the wrinkles on performance of the inspected workpiece or part.

Once an area has been fully characterized for input to stress models, the infrared thermography system can be moved to the next area to be inspected. The steps in the process can be repeated for each area until the entire composite structure has been inspected or until a structure with a thickness in the appropriate range has been inspected.

One aspect of the subject matter disclosed in detail below is a method for inspecting a composite structure comprising: (a) moving an infrared camera to a location whereat a field of view of the infrared camera encompasses an inspection area on a surface of the composite structure; (b) activating at least one flash lamp to output light that illuminates at least portions of the inspection area; (c) activating the infrared camera to acquire infrared imaging data while the field of view of the infrared camera encompasses at least the inspection area; (d) processing the infrared imaging data to create a thermal signature; and (e) determining whether the thermal signature is similar within a specified threshold to any one of a multiplicity of reference thermal signatures stored in a reference database or not, the reference thermal signatures having one or more characteristics indicating the presence of wrinkles. Step (d) may comprise calculating a first or second derivative of the infrared imaging data over time. The composite structure is accepted if the thermal signature is not similar within a specified threshold to any one of the reference thermal signatures.

The method described in the preceding paragraph may further comprise: (f) measuring a wavelength of wrinkles using infrared imaging data that is indicative of the presence of wrinkles under the surface of the inspected area; (g) retrieving a transfer function from the reference database corresponding to a reference thermal signature that is similar within the specified threshold to the thermal signature created in step (d); and (h) applying the retrieved transfer function to the measured wavelength to estimate an actual wavelength of the wrinkles, wherein steps (f) through (h) are performed if the thermal signature is similar within a specified threshold to any one of the reference thermal signatures. The method may further comprise: (i) moving an ultrasonic transducer array to a location whereat the ultrasonic transducer array can scan the inspection area on the surface of the composite structure; (j) activating the ultrasonic transducer array to transmit ultrasound waves into the composite structure in the inspection area; (k) acquiring ultrasonic imaging data representing ultrasonic echoes returned from the inspection area; (l) estimating an actual amplitude of the wrinkles based on the ultrasonic imaging data; (m) calculating a wrinkle wavelength-to-amplitude ratio using the estimated actual wavelength and estimated actual amplitude of the wrinkles; and (n) determining whether the wrinkle wavelength-to-amplitude ratio calculated in step (m) is outside an allowable range or not. In this case, the composite structure is accepted if the wrinkle wavelength-to-amplitude ratio is not outside the allowable range and rejected if the wrinkle wavelength-to-amplitude ratio is outside the allowable range. The wrinkle wavelength-to-amplitude ratio, along with orientation information, can be input into a stress model to model the impact of the wrinkles on performance of the composite structure.

Another aspect of the subject matter disclosed in detail below is a method for inspecting a composite structure comprising: (a) acquiring infrared imaging data from an inspected area on a surface of the composite structure using an infrared camera, the infrared imaging data being indicative of the presence of wrinkles under the surface of the inspected area; (b) processing the infrared imaging data to estimate a value of a first wrinkle dimensional parameter of the wrinkles under the surface of the composite structure in the inspected area; (c) subsequent to step (a), acquiring ultrasonic imaging data from the inspected area on the surface of the composite structure using an ultrasonic transducer array; (d) processing the ultrasonic imaging data to estimate a value of a second wrinkle dimensional parameter of wrinkles under the surface of the composite structure in the inspected area; (e) calculating a value of a wrinkle parameter which is a function of the first and second wrinkle dimensional parameters; and (f) determining a status of the composite structure in dependence on whether the value of the wrinkle parameter calculated in step (e) is inside or outside an allowable range of values. In some embodiments, the first wrinkle dimensional parameter is wrinkle wavelength, the second wrinkle dimensional parameter is wrinkle amplitude, and the wrinkle parameter is a ratio of wrinkle wavelength to wrinkle amplitude.

A further aspect of the subject matter disclosed in detail below is a method for measuring features in a composite structure made of a composite material and having a thickness, the method comprising: (a) establishing a reference database containing transfer functions that relate true wrinkle wavelength to measured wrinkle wavelength in a multiplicity of reference standards made of the same composite material and having the same thickness as the composite structure to be inspected, the reference database further containing, for each transfer function, associated wrinkle dimensional data representing at least known depths, amplitudes and wavelengths of wrinkles in the multiplicity of reference standards; (b) activating at least one flash lamp to output light that illuminates an area on a surface of the composite structure; (c) activating an infrared camera to acquire infrared imaging data representing a temperature of the surface of the composite structure in at least a portion of the area illuminated in step (b); (d) processing the infrared imaging data to identify the presence of wrinkles in a portion of the composite structure underneath at least a portion of the illuminated area; (e) measuring a time required to get a maximum contrast between the wrinkled portion and a surrounding non-wrinkled portion of the composite structure; (f) measuring a wavelength of wrinkles imaged by the infrared imaging data; (g) estimating a depth of the wrinkled portion based on the time measured in step (e); (h) using the estimated depth and the measured wavelength to retrieve a transfer function from the reference database; and (i) applying the retrieved transfer function to the measured wavelength to estimate an actual wavelength of the wrinkles in the wrinkled portion of the composite structure. This method may further comprise: (j) activating an ultrasonic transducer array to transmit ultrasound waves into the wrinkled portion of the composite structure; (k) acquiring ultrasonic imaging data representing ultrasonic echoes returned from the portion of the composite structure; (l) estimating an actual amplitude of the wrinkles based on the ultrasonic imaging data; (m) calculating a wrinkle wavelength-to-amplitude ratio using the estimated actual wavelength and estimated actual amplitude of the wrinkles; and (n) determining whether the wrinkle wavelength-to-amplitude ratio calculated in step (m) is outside an allowable range or not.

Some of the benefits provided by the infrared thermography (IRT) technology disclosed herein include: very rapid inspection (faster than array-based ultrasound inspection); the ability to see beneath wrinkles to quantify "good" material, thereby reducing knockdown factors and buying off more material; and IRT can be used to replace ultrasound testing in some cases where part thickness is within the IRT useful range (up to ¼" or so). In addition, IRT and ultrasonic inspection can work in tandem—IRT for providing a very fast baseline scan (that identifies wrinkles and other composite defects), and local ultrasonic scans for a follow-up, slower, more detailed scan of wrinkle regions.

Other aspects of systems and methods for using infrared thermography to characterize wrinkles in composite structures are disclosed below.

BRIEF DESCRIPTION OF THE DRAWINGS

FIG. 3A is a graph of the logarithm of the surface temperature of a typical composite panel versus the logarithm of time following exposure to a heat pulse.

FIG. 3B is a graph of the first derivative of the logarithm of the surface temperature presented in FIG. 3A versus the logarithm of time.

FIG. 3C is a graph of the second derivative of the logarithm of the surface temperature presented in FIG. 3A versus the logarithm of time.

Reference will hereinafter be made to the drawings in which similar elements in different drawings bear the same reference numerals.

DETAILED DESCRIPTION

Figure 1:
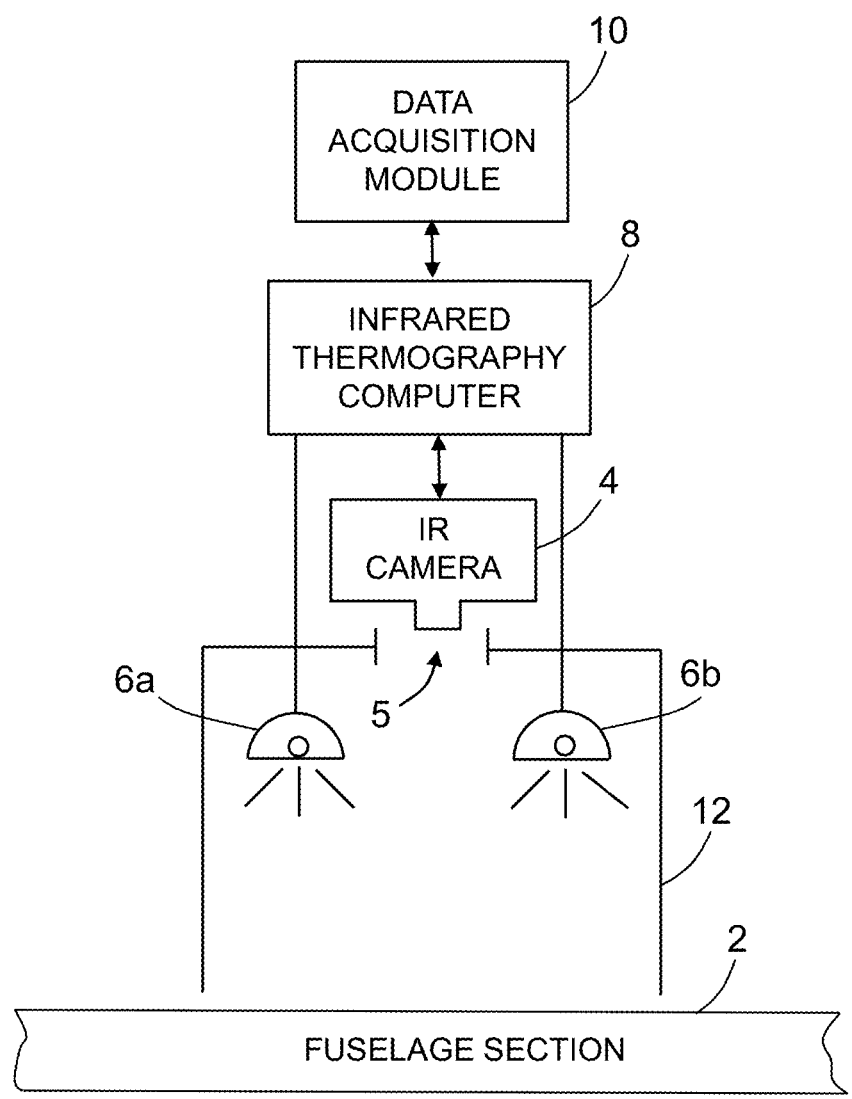
FIG. 1 is a block diagram identifying some components of a system for thermographic imaging of a fuselage section.

For the purpose of illustration, systems and methods for active (i.e., pulsed) infrared thermographic inspection of structures made of composite material (e.g., a composite laminate made of fiber-reinforced plastic) and analysis of the collected thermographic data using software tools that enable very rapid identification and quantification of wrinkles in composite structures will now be described in detail. Such systems and methods can achieve rapid infrared thermographic inspection of large composite structures (e.g., curved cylinder-like workpieces made of composite material). For the sake of illustration, systems and methods for infrared thermographic inspection of barrel-shaped (e.g., half or full barrel) fuselage sections made of composite material will be disclosed in detail below. However, it should be appreciated that the apparatus disclosed herein can be employed in the infrared thermographic inspection of large composite structures other than fuselage sections.

In accordance with embodiments disclosed in detail below, the inspection apparatus comprises flash lamps and infrared cameras, which are employed to thermographically inspect large composite structures in a non-contact, non-couplant manner. The flash lamps and infrared cameras may be supported by one or more robots that travel along tracks. As used herein, the term "tracks" encompasses rails, grooves, guide surfaces, and equivalents thereof. A track may be straight (i.e., linear) or curved. In the alternative, the flash lamps and infrared cameras could be mounted on a moving gantry (i.e., a platform that spans the composite structure and travels along parallel tracks). In this manner, the thermographic hardware (flash lamps and infrared cameras) can be moved along the surface of a composite structure to ensure access for inspection of the entire part.

Infrared thermography methods and devices make it possible to perform non-destructive testing of a material to detect defects, variations in the properties of the material, or differences in thickness of a coating or layer of the material. Infrared imaging can detect local variations in thermal diffusivity or thermal conductivity at or beneath the surface of the material.

Active thermography is used to nondestructively evaluate samples for sub-surface defects. It is effective for uncovering internal bond discontinuities, delaminations, voids, inclusions, and other structural defects that are not detectable by visual inspection of the sample. Generally, active thermography involves heating or cooling the sample to create a difference between the sample temperature and the ambient temperature and then observing the infrared thermal image that emanates from the sample as its temperature returns to ambient temperature. An infrared camera is used because it is capable of detecting any anomalies in the cooling behavior, which would be caused by sub-surface defects blocking the diffusion of heat from the sample surface to the sample's interior. More particularly, these defects cause the surface immediately above the defect to cool at a different rate than the surrounding defect-free areas. As the sample cools, the infrared camera monitors and records an image time sequence indicating the surface temperature, thereby creating a record of the changes in the surface temperature over time.

Typically, the surface of the material is heated using a flash lamp and after a fixed period of time, a thermal image is taken of the surface of the heated material. Systems for thermographic heating typically employ xenon flashtubes and off-the-shelf photographic power supplies for sample excitation. An infrared camera images the infrared spectral radiance from the surface of the material, which is representative of the temperature of the surface of the material. Differences in temperature of the surface of the material indicate differing thermal characteristics of the material. These variations in thermal characteristics of the material indicate a possible material defect or the inclusion of a foreign material.

Structural thickness and stack-up geometry needed for infrared signature processing is obtained by knowing the exact location of the infrared camera's field of view on the surface of the fuselage section.

FIG. 1 is a block diagram identifying some components of a system for thermographic imaging of a fuselage section 2. This infrared thermographic inspection system comprises a digital infrared camera 4 having a lens that is directed through a camera lens aperture 5 in a hood 12, which is designed to form a hooded enclosure adjacent to the surface being inspected. A pair of flash lamps 6a and 6b are disposed inside and in fixed spatial relationship to the hood 12. The flash lamps 6a and 6b produce flashes of light in response to trigger signals from an infrared thermography computer 8, which also controls operation of the infrared camera 4. One example of a type of infrared camera 4 suitable for use with at least some of the embodiments disclosed herein includes a focal plane array device configured to act as a spectral radiometer. Further details concerning other components that may be included in a flash lamp assembly of a type comprising an infrared camera, a pair of flash lamps and a hood can be found, for example, in U.S. Pat. No. 7,186,981.

In accordance with one method of thermographic inspection, first the flash lamps 6a and 6b are triggered to transfer heat to the composite material of the fuselage section 2. Preferably, during cooling of the composite material, the infrared camera 4 is triggered periodically to capture successive digital images of the varying spectral radiance of the heated portion of the fuselage section 2. Preferably, the thermally excited (heated) region of the composite material being inspected will cool monotonically after the excitation source removed until the sample reaches thermal equilibrium with its surroundings. The thermal response of any point on the surface of the composite material during the time interval immediately after heating will decay in such a manner that the natural logarithm of the temperature-time response of a defect-free sample, as it cools, is a function that can be approximated by a straight line.

The digital infrared imaging data captured by infrared camera 4 is received by the infrared thermography computer 8 for processing. The infrared thermography computer 8 is programmed to process infrared imaging data to detect and locate material anomalies. The infrared imaging data may be displayed on a display monitor (not shown in FIG. 1), which may be integrated with or separate from infrared thermography computer 8.

In accordance with the embodiment depicted in FIG. 1, the infrared thermography computer 8 may have digital image acquisition capabilities to convert the infrared imaging data from the infrared camera 4 to a format that can be analyzed and mathematically manipulated by the infrared thermography computer 8. An optional data acquisition module 10 may be incorporated in or separate from (as depicted in FIG. 1) the infrared thermography computer 8.

The data acquisition module 10 may be used if the infrared camera 4 captures multiple spatially different images to generate a complete mosaic image of the surface of the composite structure when the latter is too large to fit in a single image frame. The infrared thermography computer 8 may be further programmed to analyze the infrared imaging data captured by the infrared camera 4. In particular, the time history of the surface temperature response of the fuselage section 2 as it returns to room temperature can be analyzed to detect the presence of defects in the composite material.

In the context of the specific application of inspecting fuselage sections, a non-destructive inspection system may comprise means for scanning the skin of the fuselage section from a vantage point external to the fuselage section and means for scanning substructure, such as stiffeners attached to the inside of the fuselage section. The means for scanning stiffeners on the inside of a fuselage section can work in concert and concurrently with the means that scan the fuselage section externally. In the alternative, the external and internal scanning can be performed at different times and/or at different places. The fuselage sections can be scanned externally before or after the stiffeners have been attached. In the embodiments disclosed below, the internal scanning means comprise ultrasonic transducer arrays, while the external scanning means comprise infrared cameras.

Figure 2:
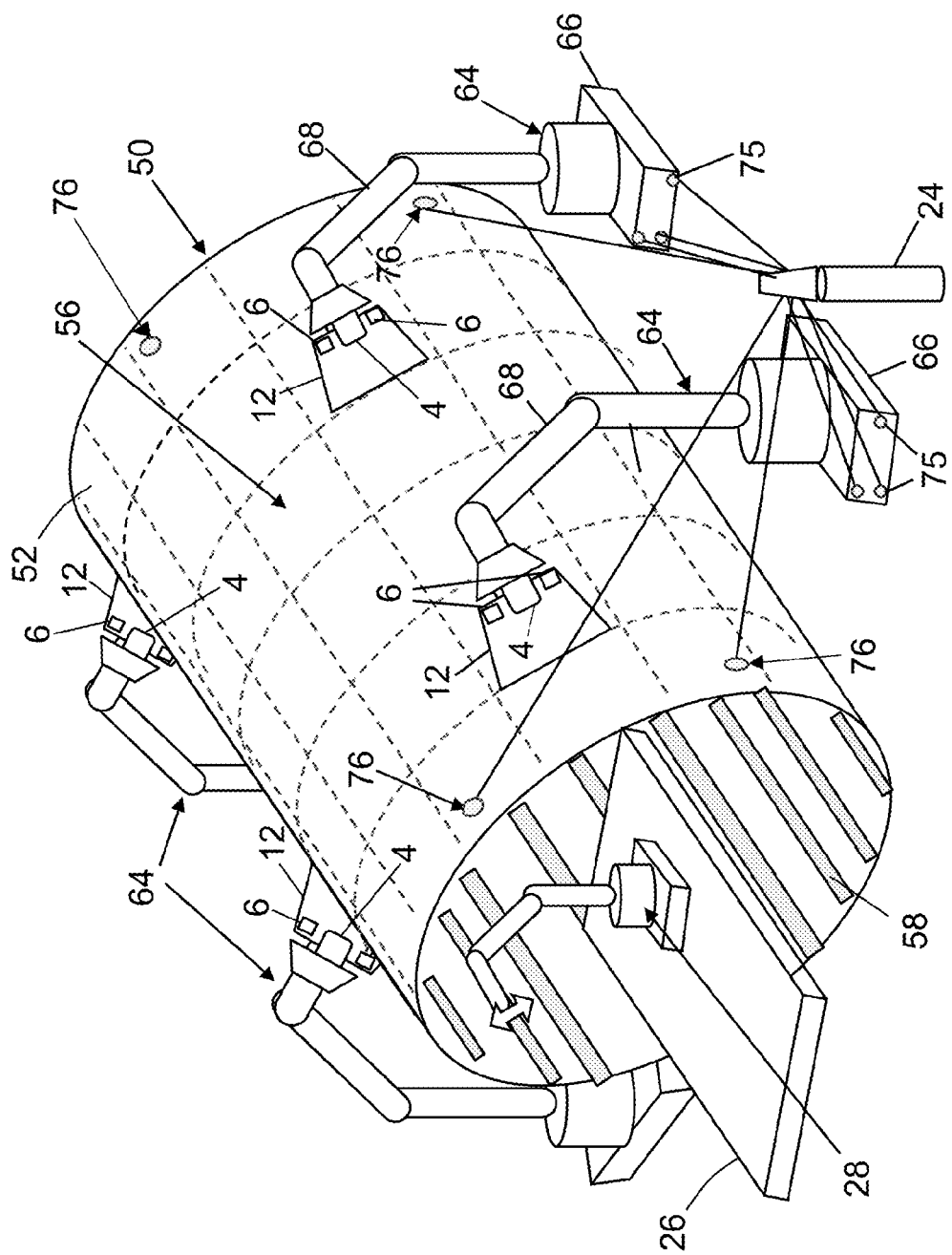
FIG. 2 is a diagram representing an isometric view of a full-barrel fuselage section being inspected by an infrared thermographic inspection system having multiple robots in accordance with one embodiment. A laser tracker determines the locations of the robots relative to the fuselage section using optical targets attached to the fuselage section and to the robot bases.

FIG. 2 depicts a full-barrel fuselage section 50 being inspected by a non-destructive inspection system comprising multiple robots 64 equipped with infrared thermography assemblies in accordance with one embodiment. Each robot 64 comprises a movable robot base 66 and an articulated robotic arm 68 having a proximal end coupled to the robot base 66. Each robot base 66 may be mounted to a mobile holonomic crawler vehicle or coupled to a linear track (not shown in FIG. 2). A respective infrared thermography assembly is coupled to a distal end of each robotic arm 68. Each infrared thermography assembly comprises an infrared camera 4 and two or more flash lamps 6 attached inside a hood 12. Each hood 12 may be sized to cover a respective square area 56 on the outer surface 52 of the fuselage section 50. The infrared imaging data acquired from adjacent square areas 56 can be stitched together based on measurements of the respective locations of the robot base 66 using a laser tracker 24 and respective movements of the robotic arms 68 using encoders incorporated in the robot 64. The stitching 60 process may be performed on a real-time basis or may be performed at a later time.

In accordance with one embodiment, a laser tracker 24 is used to determine the locations of the robot bases 66 relative to the fuselage section 50. This is accomplished using optical targets 75 attached to the robot bases 66 and optical targets 76 attached to the fuselage section 50. Optical targets 76 may comprise spherically mounted retroreflectors, which will be described in more detail below. The optical targets 76 may be inserted in holes formed at predetermined locations about the outer surface 52 of the fuselage section 50. The holes in the fuselage section 50 may be components of a part reference system, such as a determinant assembly coordinate system, in which parts are referenced to each other (as opposed to the parts being referenced to assembly tooling). The part reference system suitably indexes the location of each of the holes in three dimensions.

The system depicted in FIG. 2 can be used to acquire infrared imaging data representing characteristics of the internal structure of the composite material. The acquired infrared imaging data can be processed in a different ways using the following equations:

$$\Delta T(t) = \frac{Q}{e\sqrt{\pi t}}$$

$$e = \sqrt{k\rho C}$$

$$\ln(\Delta T) = \ln\left(\frac{Q}{e\sqrt{\pi}}\right) - 0.5\ln(t)$$

where T is surface temperature; t is time; e is the thermal effusivity or resistance to heat flow; Q is the input energy; k is the thermal conductivity; p is the density; and C is the heat capacity. A low thermal effusivity means that diffusing heat travels quickly through the material (e.g., metals), so that the temperature change across the thickness of the material is small; a high thermal effusivity means that diffusing heat travels slowly through the material (e.g., composites), so that the temperature change across the thickness of the material is large.

Figure 3:
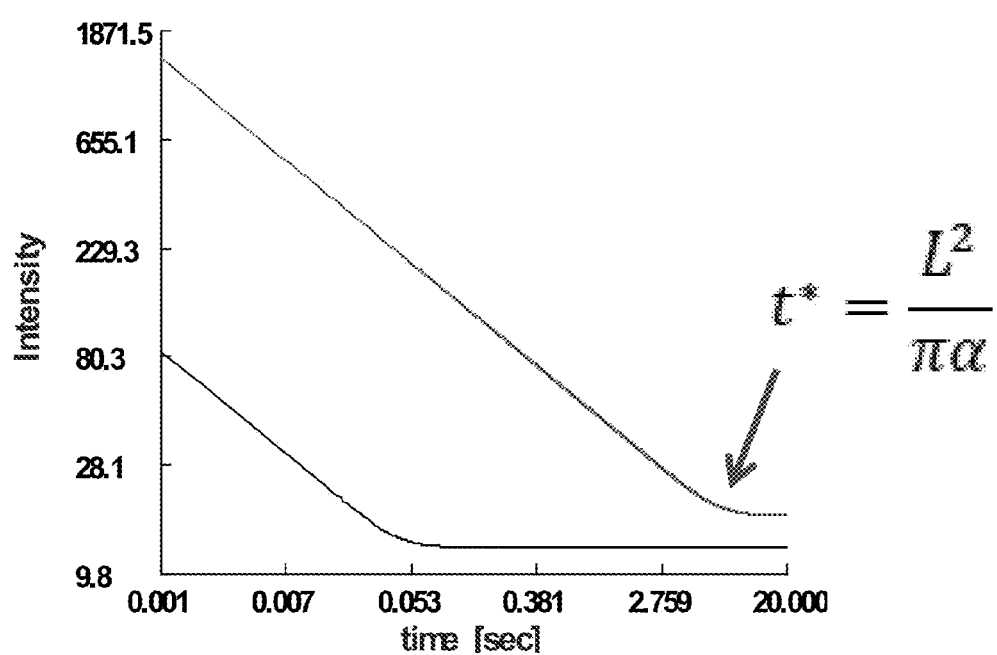
FIG. 3 is a graph of intensity (i.e., surface temperature) versus time (using logarithmic scales) for two composite panels following exposure to a heat pulse.

FIG. 3 is a graph of intensity (i.e., surface temperature) versus time (using logarithmic scales) for two composite panel samples following exposure to a heat pulse. The break from a slope of −0.5 indicates that the diffusing heat has reached an interface. The thickness L of the material can be calculated based on the time t* at which that break occurs using the following equation:

$$t^* = \frac{L^2}{\pi\alpha}$$

where α is the thermal diffusivity or rate of heat flow (α=k/ρC);

FIG. 3A is a graph of the logarithm of the surface temperature of a typical composite panel versus the logarithm of time following exposure to a heat pulse. FIG. 3B is a graph of the first derivative of the logarithm of the surface temperature presented in FIG. 3A versus the logarithm of time. FIG. 3C is a graph of the second derivative of the logarithm of the surface temperature presented in FIG. 3A versus the logarithm of time. These curves spread when the composite material underneath the surface area exposed to the heat pulse during infrared thermography contains wrinkles.

Figure 4A:
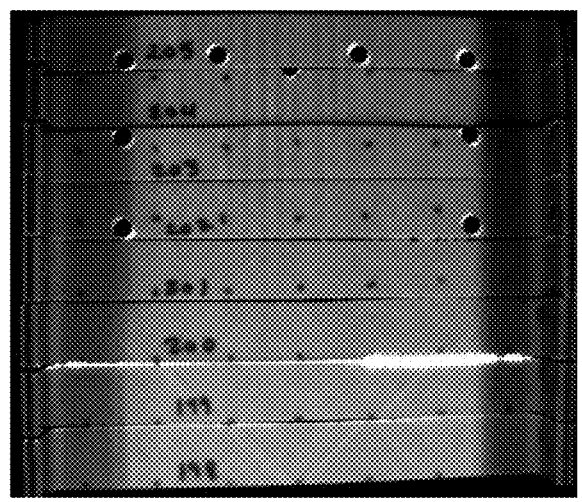
FIG. 4A is a raw infrared image of a wrinkled composite specimen.
Figure 4B:
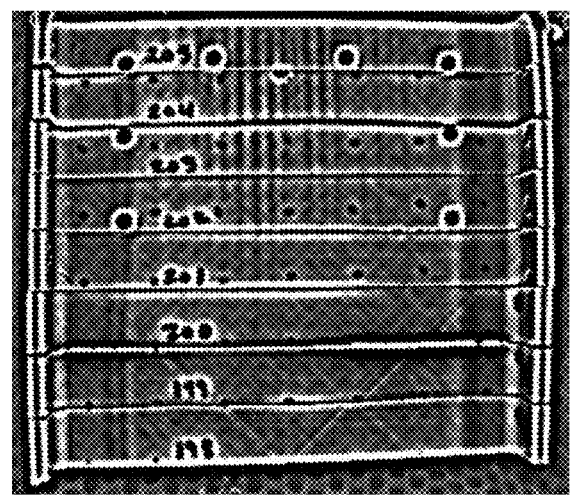
FIG. 4B shows the result when the raw infrared image shown in FIG. 4A is high-pass filtered.
Figure 4C:
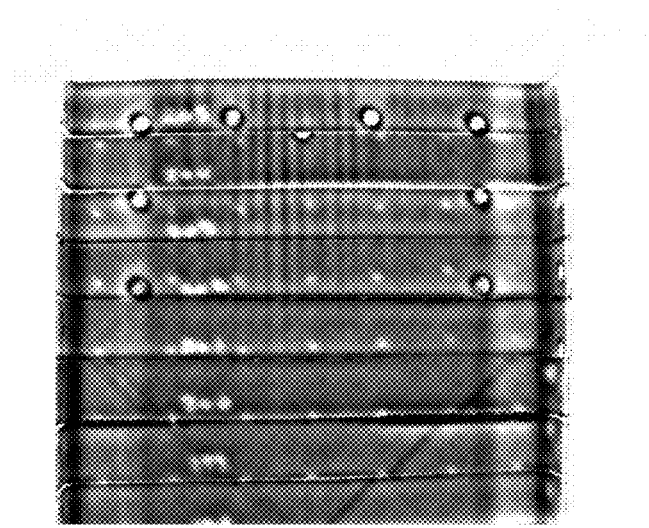
FIG. 4C shows the result when the raw infrared image shown in FIG. 4A is undergoes first-derivative processing.
Figure 4D:
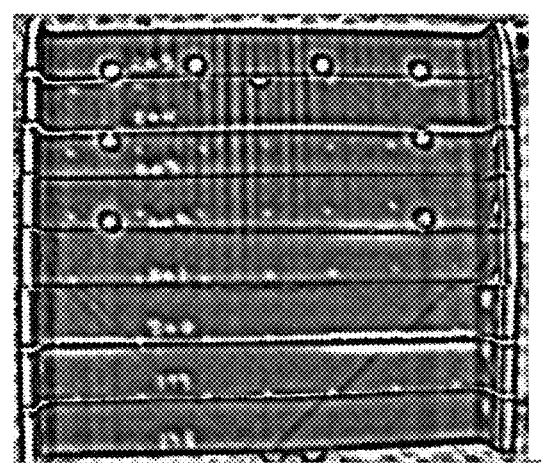
FIG. 4D shows the result when the first-derivative infrared image shown in FIG. 4C is high-pass filtered.
Figure 4E:
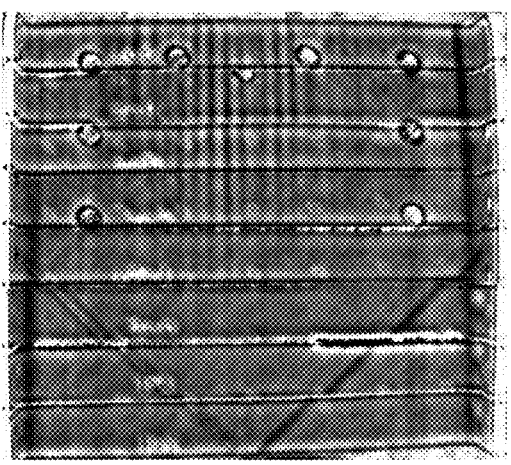
FIG. 4E shows the result when the first-derivative infrared image shown in FIG. 4C is undergoes second-derivative processing.
Figure 4F:
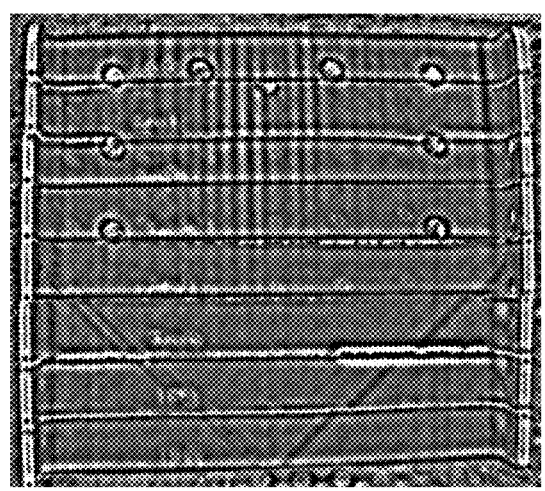
FIG. 4F shows the result when the second-derivative infrared image shown in FIG. 4E is high-pass filtered.

FIGS. 4A through 4F present infrared imaging data acquired from wrinkled composite specimens. Data was collected with an infrared imaging camera, such as an infrared camera available from Thermal Wave Imaging, Inc. (Ferndale, Mich.). Data collected by a Thermal Wave Imaging infrared camera may be processed using a known thermographic signal reconstruction (TSR) method. The images seen in FIGS. 4A through 4F show that wrinkles are detectable very rapidly using infrared thermography. FIG. 4A is a raw infrared image of a wrinkled composite specimen. FIG. 4B shows the result when the raw infrared image shown in FIG. 4A is high-pass filtered. FIG. 4C shows the result when the raw infrared image shown in FIG. 4A undergoes first-derivative processing. FIG. 4D shows the result when the first-derivative infrared image shown in FIG. 4C is high-pass filtered. FIG. 4E shows the result when the first-derivative infrared image shown in FIG. 4C undergoes second-derivative processing. FIG. 4F shows the result when the second-derivative infrared image shown in FIG. 4E is high-pass filtered.

Figure 5B:
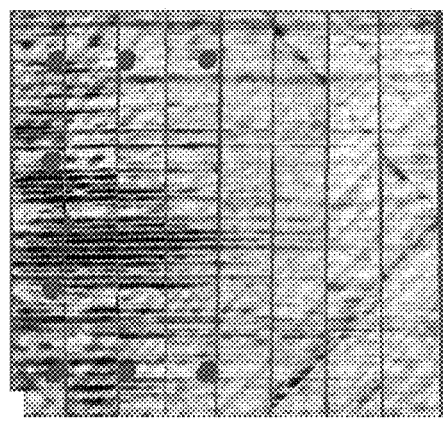
FIG. 5B is an ultrasonic image of the same wrinkled composite specimen having the raw infrared image shown in FIG. 4A.
Figure 5A:
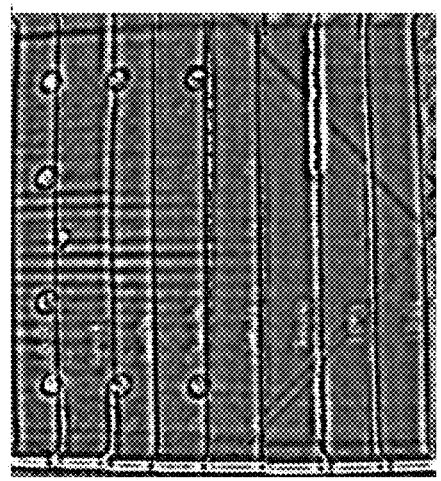
FIG. 5A shows the result when the raw infrared image shown in FIG. 4A is subjected to second derivative processing and high-pass filtering.

FIGS. 5A and 5B show that infrared images acquired using high-pass filtering are comparable to an ultrasonic image. FIG. 5A shows the result when the raw infrared image shown in FIG. 4A is second derivative processed and high-pass filtered. FIG. 5B is an ultrasonic image of the same wrinkled composite specimen. Thus, a rapid infrared thermography inspection technique could be used to identify wrinkles, with local follow-up using the slower ultrasonic inspection technique only if wrinkles are found.

Figure 6:
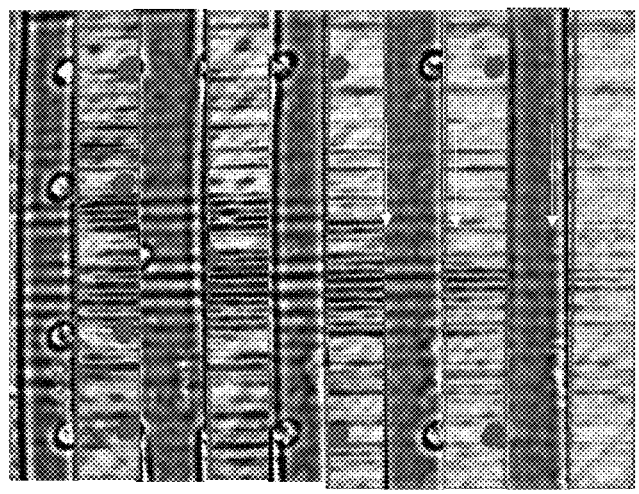
FIG. 6 is an interleaved combination of individual coupons from the infrared image seen in FIG. 5A and from the ultrasonic image seen in FIG. 5B. The individual coupons are compared directly, with one on top of the other.

FIG. 6 also shows that infrared images acquired using high-pass filtering are comparable to an ultrasonic image. FIG. 6 is an interleaved combination of individual coupons from the infrared image seen in FIG. 5A and from the ultrasonic image seen in FIG. 5B. The individual coupons are compared directly, with one on top of the other.

Wrinkles can be imaged from both sides (OML and IML) of a composite part. High intensity on one side corresponds to low intensity on the opposite side. There will be cooler temperature measurement at wrinkle peak, where there is a higher fiber/resin ratio, and hotter temperature measurement at wrinkle valley, where there is a lower fiber/resin ratio.

Off-the-shelf software can be modified to do a search routine for finding wrinkles by creating thermal signatures that can be used to rapidly and automatically indicate the presence of wrinkle indicia in an infrared image and then starting a process to find and quantify those wrinkles by comparing the acquired thermal signatures to reference thermal signatures stored in a reference database. The hardware where the reference database resides is a non-transitory tangible computer-readable medium.

Figure 7A:
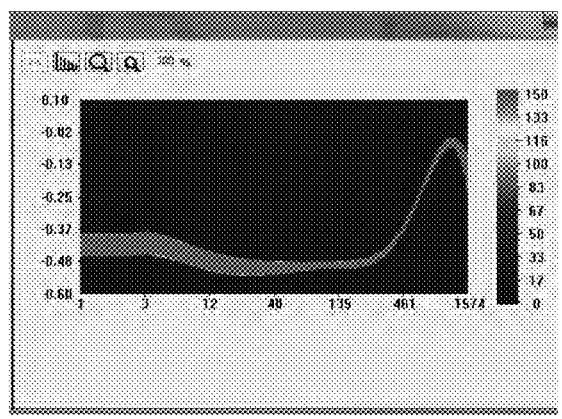
FIG. 7A is a screenshot from a display monitor which includes display of a graph of the first derivative of the surface temperature in a wrinkle-free region of a composite panel versus time (using logarithmic scales) for all pixels corresponding to that wrinkle-free region, the result being referred to herein as a "no wrinkle signature". (Although not apparent from FIGS. 7A-7C, in actuality such signatures may be displayed in color.)

FIG. 7A is a screenshot from a display monitor which includes display of a graph of the first derivative of the surface temperature in a wrinkle-free region of a composite panel versus frame number (using logarithmic scales) for all pixels corresponding to that wrinkle-free region, the result being referred to herein as a "no wrinkle signature". (Although not apparent from FIGS. 7A-7C, in actuality such signatures are may be displayed in color.)

Figure 7B:
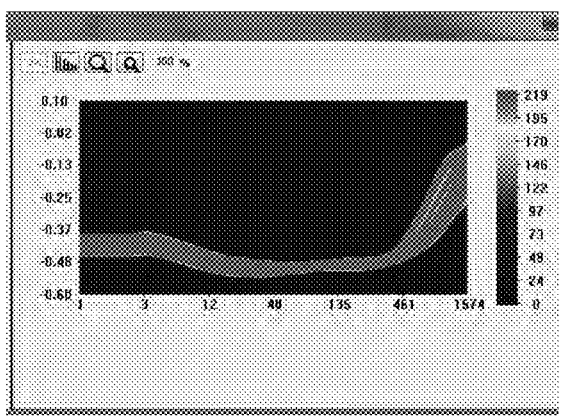
FIG. 7B is a screenshot from a display monitor which includes a graph of the first derivative of the surface temperature in a wrinkled region of the same composite panel versus time (using logarithmic scales) for all pixels corresponding to that wrinkled region, the result being referred to herein as a "wrinkle signature".

FIG. 7B is a screenshot from a display monitor which includes a graph of the first derivative of the surface temperature in a wrinkled region of the same composite panel versus frame number (using logarithmic scales) for all pixels corresponding to that wrinkled region, the result being referred to herein as a "wrinkle signature".

Figure 7C:
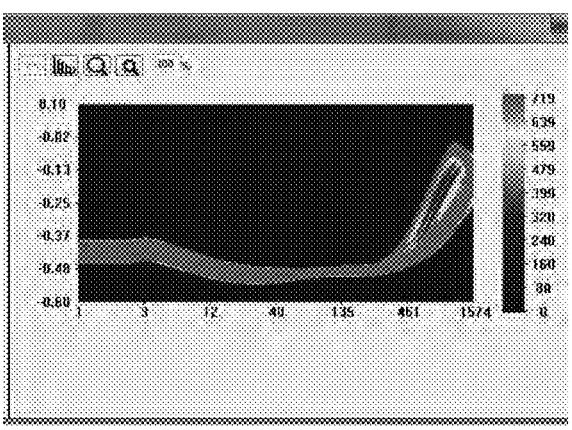
FIG. 7C is a screenshot from a display monitor which includes a graph of the first derivative of the surface temperature versus time (using logarithmic scales) when the wrinkle and wrinkle-free signatures are superimposed for the purpose of automatic defect recognition.

FIG. 7C is a screenshot from a display monitor which includes a graph of the first derivative of the surface temperature versus frame number (using logarithmic scales) when the wrinkle and wrinkle-free signatures are superimposed for the purpose of automatic defect recognition.

In each of FIGS. 7A through 7C, the horizontal axis is the number of image frames acquired after the flash lamp is activated. Frames can be converted to time by dividing by the frame rate of the camera. The typical frame rate is 60 or 120 Hz, but can be changed if required to permit longer examination times. The superposition of the wrinkle/no wrinkle signatures seen in FIG. 7C occurs when those two regions of interest are combined. For automatic defect recognition purposes, one would expect to see the no wrinkle signature. If the wrinkle signature occurs, then it is obvious that there is a wrinkle in the composite part under test.

One method for detecting and characterizing wrinkles in composite material uses a combination of infrared thermographic inspection and ultrasonic inspection. First, infrared thermography can be used to identify the presence of a wrinkle using thermal signatures. The wavelength of the wrinkle can be measured using infrared image processing. Thermography can measure the wavelength, but cannot measure the amplitude. So, if a rapid thermography detection is made, a more time-consuming special ultrasonic scan could be performed to assess the amplitude. More specifically, once an area having wrinkles has been located using infrared thermography and the wavelength of the wrinkles are estimated, an ultrasonic transducer array can be used to scan the identified region of interest to acquire ultrasonic imaging data including the amplitude of the wrinkles.

The infrared imaging data captured by the infrared cameras can be processed to detect internal defects, particularly wrinkles, in composite structures. A computer system can be programmed to locate and quantify those types of anomalies based on at least the infrared imaging data. The system can collect infrared imaging data for detecting wrinkles over large surface areas of the composite structure very rapidly and also quantifying a dimensional parameter of the wrinkles identified.

The systems and methods disclosed in detail below apply flash thermography equipment and software (e.g., software commercially available from Thermal Wave Imaging, Inc., Ferndale, Mich.) in defined ways to identify and measure wrinkles. The infrared camera records the surface temperature as an applied heat pulse diffuses into the surface of the part. The image acquisition time is adjusted to match the thickness and thermal properties of the material under test. Temperature versus time profiles for all pixels in the field of view are calculated, enabling thermal signatures to be produced. By comparing the thermal signature of the part under test with the thermal signature of a reference representing a similar part having wrinkles, the presence of wrinkles can be detected. For example, the thermal signature may be based on a logarithmic first derivative of temperature versus time (i.e., $d[\ln(T)]/d[\ln(t)]$) for each pixel in a selected area on the surface of the part. In accordance with some embodiments, the thermal images are enhanced by viewing an image created by intensities related to the second derivative (i.e., $d^2[\ln(T)]/d^2[\ln(t)]$) and applying a high pass filter to the image.

The wrinkle wavelength can be determined by measuring the infrared image and applying a correction factor (referred to hereinafter as a "transfer function") that accounts for any effects of the configuration of the composite part being measured (such as the heat loss or smearing of the thermal data in thicker composite parts). If the geometric information acquired using infrared thermography does not reach a certain quality factor (for a quality prediction) or is incomplete or needs to be further quantified, an ultrasonic transducer array probe running wrinkle quantification software can be rotated into position and scanned over the wrinkle area. The ultrasonic imaging data can be combined with the infrared imaging data to enable an improved quantification of the wrinkle geometry. (The infrared imaging data may provide information about the amount of good material under a wrinkle that the ultrasonic imaging data cannot provide.) More specifically, ultrasonic inspection can be used to generate digital data representing a 3-D model of a wrinkle that has been previously detected using infrared thermography. The wrinkle amplitude D could then be determined based on that 3-D model. Then the ratio L/D along a wrinkle line can be estimated. That information can be sent, along with orientation information, to a plug-in for a finite element-based stress model using structural codes or to a stress analyst to determine the impact of the wrinkles on performance of the inspected workpiece or part.

It may also be possible to generate a so-called "thermal B-scan" image which could be used to estimate the amplitude (i.e., height) of the wrinkle. The thermal B-scan could be automatically checked for indications that there is "good" material underneath the wrinkle. Using this information, it may possible to estimate the wrinkle amplitude D and wrinkle thickness T (i.e., the number of plies of the composite laminate which are disoriented).

Once an area has been fully characterized for input to stress models, the infrared thermography system can be moved to the next area to be inspected. The steps in the process can be repeated for each area until the entire composite structure has been inspected or until a structure with a thickness in the appropriate range has been inspected.

In accordance with some embodiments, the IRT wrinkle wavelength measurement process employs a standard thermal signature database comprising respective sets of standard thermal signatures acquired from composite material of different known thicknesses having wrinkles of known size and shape. Preferably, reference standards of composite material can be fabricated which have artificial wrinkles with known dimensions (i.e., known wavelength, amplitude, thickness, and depth). In the alternative, a range of wrinkles can be gathered from production.

Figure 8:
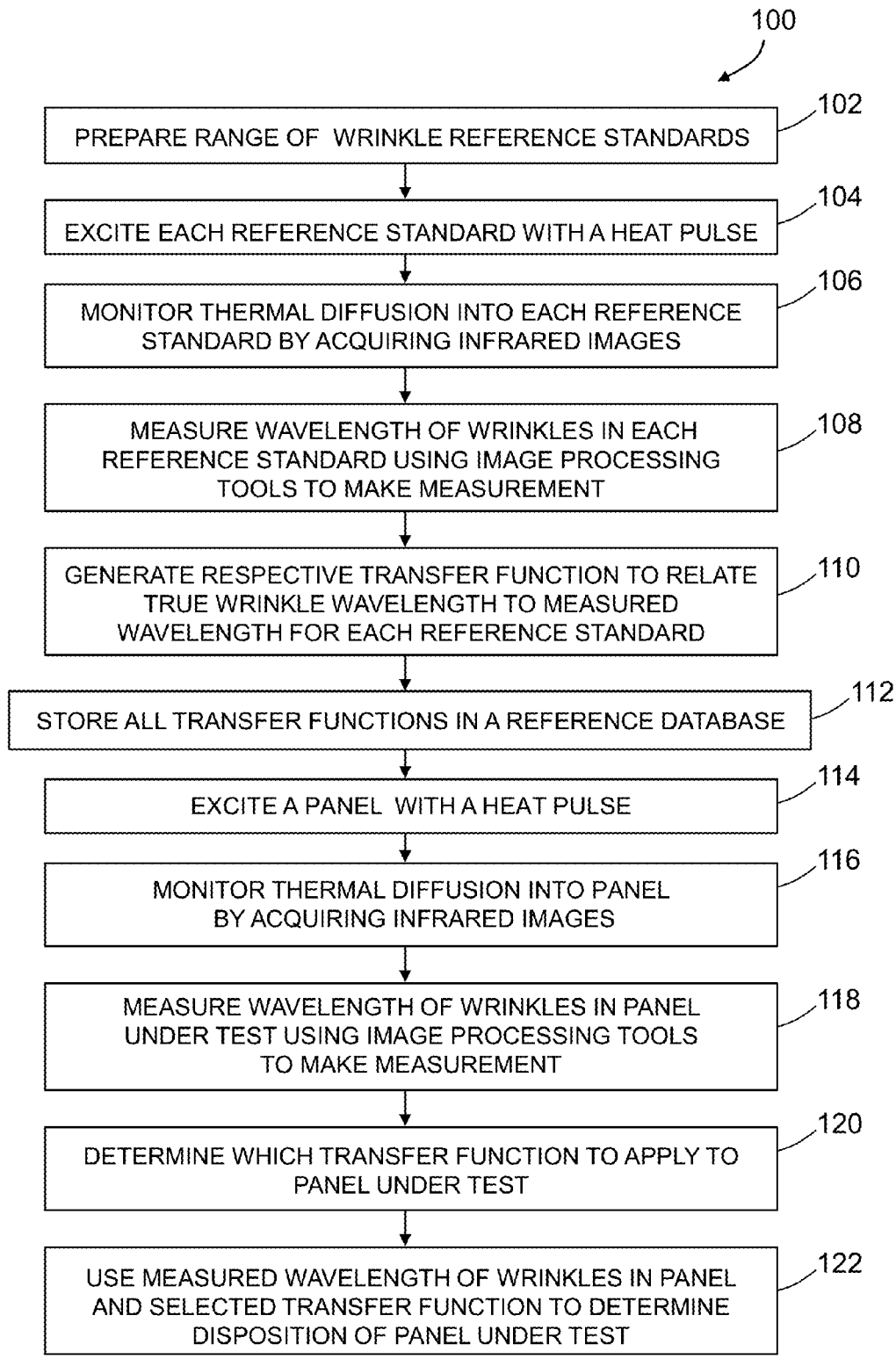
FIG. 8 is a flowchart identifying steps of a method for infrared thermographic inspection in accordance with some embodiments.

FIG. 8 is a flowchart identifying steps of a method 100 for infrared thermographic inspection in accordance with some embodiments. Before inspection is started, a multiplicity of reference standards having wrinkles with a range of amplitudes, wavelengths and depths are prepared (step 102), e.g., by fabrication of reference standards having wrinkles with programmed (i.e., known) amplitude and wavelength or by collecting production samples. In the alternative, one could use micro-sectioned parts with wrinkles in the absence of a wrinkle standard.

Each reference standard is then excited with a heat pulse (step 104). Subsequent thermal diffusion of heat into each reference standard in monitored by acquiring infrared images (step 106). Wrinkles disrupt the heat flow. Although the thickness of material can be constant, the orientation of the fibers and the localized resin content disrupt the flow in different ways. At locations where the out-of-plane distortion of the fibers is nearest the surface monitored by the infrared camera, the surface will be cool. At locations where the resin pool (caused by the wrinkle) is closest to the surface, the surface will be hot. After the raw infrared images have been captured, they are stored in a reference database. In many cases, it is recommended that the raw infrared imaging data be processed with a method such as first-derivative processing. In addition, the first-derivative imaging data can be processed using second-derivative processing. All of this imaging data is stored in the reference database.

Still referring to FIG. 8, using either the first- or second-derivative imaging data, the wavelength of the wrinkles in each reference standard is measured using image processing tools to make the measurement in a well-known manner (step 108). (Preferably the wavelength is measured from one positive peak to another positive peak in the wrinkles.) The available range of wrinkle specimens can be used to define the minimum detectable wrinkle amplitude and wavelength. There is a minimum amplitude that cannot be detected, since the out-of-plane distortion is too small to cause the surface temperature variation. This amplitude sets the detectable amplitude. As long as the minimum amplitude is above the detection threshold, the necessary wrinkles can be detected and the rest ignored. High-pass filters can be used to enhance the detail of the waves during the measurement.

Based on the measurement data, a respective transfer function can be generated to relate true (i.e., known) wrinkle wavelength to measured wavelength for each reference standard (step 110). It is likely that the transfer function will be dependent on the distance from the surface to the wrinkle (i.e., wrinkle depth), since lateral heat transfer occurs preferentially in the plane of the part (e.g., in the CFRP fiber direction). All transfer functions are stored in the reference database (step 112).

After the reference database has been established, it can be referred to during IRT inspection of workpieces and parts made of composite material. For the purpose of illustration, IRT inspection of a panel made of composite material will now be described. Inspection of the panel follows the same procedure as for a reference standard, except the calibration information gathered with the reference standard will be used to disposition the wrinkle and assess whether it exceeds allowable limits or warrants further inspection with ultrasonic transducers.

Referring again to FIG. 8, the panel to be inspected is excited with a heat pulse by activating the flash lamps (step 114). The resulting thermal diffusion into the panel under test is then monitored by acquiring successive infrared images over time (step 116). Those raw infrared images can be processed in the same manner that the raw infrared images acquired from the reference standards were processed, e.g., using first- and second-derivative processing. Using either the first- or second-derivative imaging data, the wavelength of the wrinkles in each reference standard is measured using image processing tools to make the measurement in a well-known manner (step 118). Then a determination is made which transfer function to apply to the panel under test (step 120).

It is expected that the wavelength signal will become fuzzier with increasing depth. By measuring the time required to get the maximum contrast between the wrinkled area and the surrounding non-wrinkled area, one can estimate the depth of the wrinkle. With the depth information, one can determine which transfer function to use, for example, by inputting the wrinkle wavelength and wrinkle depth into a look-up table which correlates transfer functions with wrinkle depths, amplitudes and wavelengths.

Using the measured wavelength and estimated depth of the wrinkles in the panel and the selected transfer function, the actual (i.e., true) wrinkle wavelength in the panel can be calculated. For a given wrinkle wavelength, measured wavelength will likely increase with distance from the surface (i.e., with increasing depth). The actual wrinkle wavelength can be used to determine the disposition of the panel under test (step 122), e.g., whether the wrinkled region on the panel should undergo high-resolution ultrasonic inspection or not. In some cases, the actual wrinkle wavelength determined using infrared thermography may be sufficient to determine disposition of the part without need of ultrasonic inspection.

Even if IRT inspection is used without any quantitative capability, the speed at which an IRT system could screen a panel for wrinkles makes it an advantage—even if a separate high-resolution ultrasonic scan is performed to help quantify the wrinkle. (Such high-resolution ultrasonic scans are not currently performed and the traditional ultrasonic scans cannot detect wrinkles.) Currently available IRT equipment has fields of view of 16 to 36 square feet with acquisition times dependent on the maximum thickness of the panel to be inspected and with inspection times on the order of 30 seconds or less.

If a determination is made, based on the results of the IRT inspection, that the panel should also undergo high-resolution ultrasonic inspection in an area having wrinkles, an ultrasonic transducer array can be used to scan the identified region of interest to acquire ultrasonic imaging data. That ultrasonic imaging data can be processed to determine the amplitude of the wrinkle using the three-dimensional modeling technique disclosed in U.S. patent application Ser. No. 14/049,974, the disclosure of which is incorporated by reference herein in its entirety.

Using the results of IRT inspection, high-resolution ultrasonic inspection, or both, a determination can be made whether the panel has wrinkle dimensions which exceed the allowable values. There are allowable values for wrinkles. The values vary depending on the type of part. The typical allowables are described in terms of L/D (i.e., wavelength/amplitude). Panels having wrinkles characterized by an L/D ratio outside an allowable range may be rejected.

Even without direct measurement of amplitude, useful data can be obtained since the threshold wrinkle depth and wrinkle amplitude will provide threshold values for minimum detectable wavelength at the maximum detectable depth. It is likely the detectable wavelength will decrease as the wrinkle depth decreases.

Figure 9:
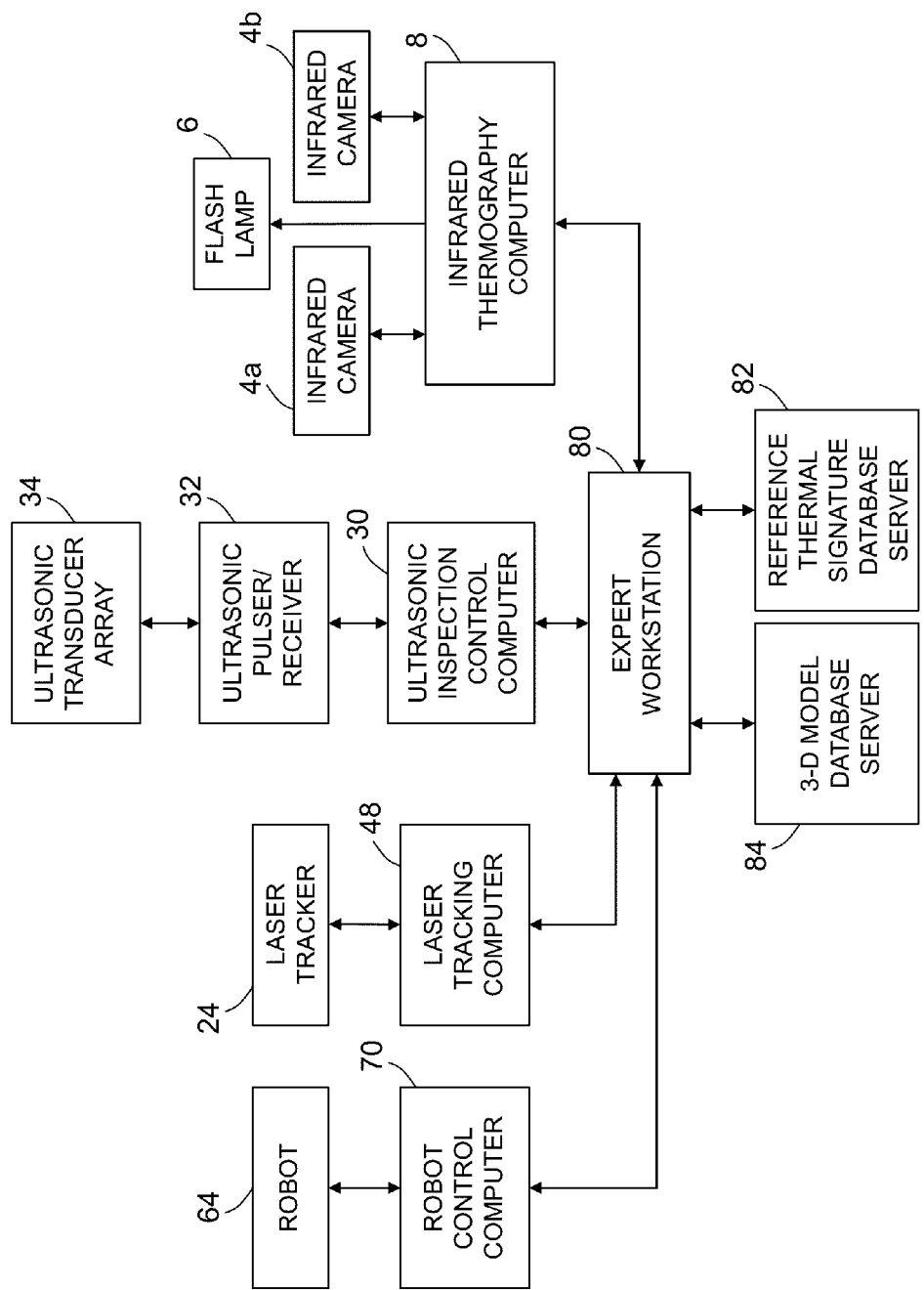
FIG. 9 is a block diagram identifying some components of a system for non-destructive inspection of large composite structures in accordance with some embodiments.

FIG. 9 is a block diagram identifying some components of a system for non-destructive inspection of large-scale composite structures in accordance with one architecture. Movements of the robot 64 (on which infrared cameras 4a, 4b and flash lamp 6 are mounted) are controlled by a robot control computer 70. Movements and firing of the laser tracker 24 are controlled by a laser tracking computer 48, which also receives laser tracking data from the laser tracker 24. Activation of the flash lamps 6 and activation of the infrared cameras 4a and 4b are controlled by an infrared thermography computer 8, which also receives infrared imaging data from the infrared cameras 4a and 4b. Activation of an ultrasonic transducer array 34 is controlled by an ultrasonic inspection control computer 30.

All of the computers can be in wireline or wireless communication with a master computer at an expert workstation 80. The master computer at the expert workstation 80 may be programmed to correlate the infrared imaging data with the laser tracking data and with the ultrasonic imaging data. The master computer may be further programmed to request 3-D model data from a 3-D model database server 84. In the case of thermographic wrinkle characterization, the master computer at the expert workstation 80 may also be programmed to request reference thermal signature data from a reference thermal signature database server 82.

The laser tracking computer 48 acquires location data for the infrared cameras 4a and 4b in a 3-D coordinate system of the composite structure. In the case of a barrel-shaped fuselage section, the infrared imaging data can be mapped directly onto a 3-D model of the fuselage section. The overlay of infrared imaging data with the 3-D model data enables improved data analysis and potential automated data analysis as well. For example, features/anomaly indications can be directly correlated to the fuselage structure by direct overlay of infrared imaging data on the 3-D model. In addition, the direct data overlay onto the model can be used to determine the thickness of a local area or spatial point. In one embodiment, the process involves application of infrared imaging data strips as one or more computer graphics texture maps, which are projected onto the 3-D model surfaces in a virtual environment displayed on a monitor or computer screen at the expert workstation 80.

In the embodiment depicted in FIG. 9, ultrasonic inspection is performed using an ultrasonic transducer array 34, which can be mounted on the end of an articulated arm of a robot similar to robot 64. The ultrasonic inspection system further comprises an ultrasonic pulser/receiver unit 32 which is operatively coupled to the ultrasonic transducer array 34 and encoding means (not shown). The ultrasonic pulser/receiver unit 32 is programmed to perform the following operations: sending control signals to the ultrasonic transducer array 34; receiving scan data signals from the ultrasonic transducer array 34; receiving X-Y position data signals from the encoding means; and correlating the scan data with the X-Y position data.

The ultrasonic inspection control computer 30 may comprise a general-purpose computer programmed with nondestructive inspection (NDI) scanning application software. The ultrasonic pulser/receiver unit 32 sends the encoder pulses to the NDI scanning software application, which interprets the encoder pulses as X- and Y-encoder values, which are used to position the scan data from the ultrasonic array 34 in the proper locations. The ultrasonic inspection control computer 30 can transmit ultrasonic imaging data to the expert workstation 80. The display may involve application of ultrasonic imaging data strips as one or more computer graphics texture maps, which are projected onto the 3-D model surfaces in a virtual environment displayed on a monitor or computer screen at the expert workstation 80.

Figure 10:
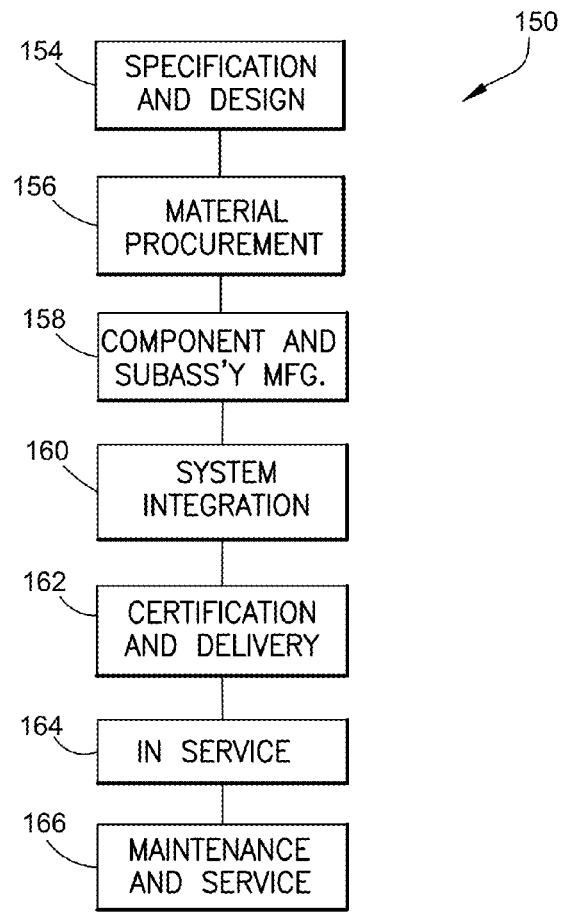
FIG. 10 is a flow diagram of an aircraft production and service methodology.
Figure 11:
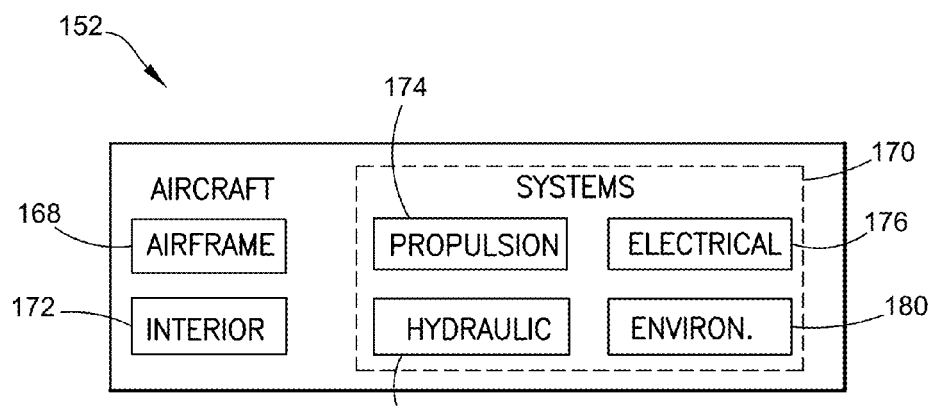
FIG. 11 is a block diagram showing systems of an aircraft.

The systems and methods disclosed above may be employed in an aircraft manufacturing and service method 150 as shown in FIG. 10 for inspecting parts of an aircraft 152 as shown in FIG. 11. During pre-production, exemplary method 150 may include specification and design 154 of the aircraft 152 and material procurement 156. During production, component and subassembly manufacturing 158 and system integration 160 of the aircraft 152 takes place. Thereafter, the aircraft 152 may go through certification and delivery 162 in order to be placed in service 164. While in service by a customer, the aircraft 152 is scheduled for routine maintenance and service 166 (which may also include modification, reconfiguration, refurbishment, and so on).

Each of the processes of method 150 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 11, the aircraft 152 produced by exemplary method 150 may include an airframe 168 (comprising, e.g., a fuselage, frames, stiffeners, wing boxes, etc.) with a plurality of systems 170 and an interior 172. Examples of high-level systems 170 include one or more of the following: a propulsion system 174, an electrical system 176, a hydraulic system 178, and an environmental control system 180. Any number of other systems may be included. Although an aerospace example is shown, the principles disclosed herein may be applied to other industries, such as the automotive industry.

Apparatus and methods embodied herein may be employed during any one or more of the stages of the production and service method 150. For example, components or subassemblies fabricated or assembled during production process 158 may be inspected using the infrared thermographic inspection system disclosed herein. Also, one or more apparatus embodiments, method embodiments, or a combination thereof may be utilized during the production stages 158 and 160, for example, by substantially expediting nondestructive inspection of or reducing the cost of an aircraft 152. Similarly, one or more of apparatus embodiments, method embodiments, or a combination thereof may be utilized while the aircraft 152 is in service, for example and without limitation, during maintenance and service 166.

While infrared thermographic inspection methods have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude two or more steps or portions thereof being performed concurrently or to exclude any portions of two or more steps being performed alternatingly.

The invention claimed is:

1. A method for inspecting a composite structure comprising:
    (a) moving an infrared camera to a location whereat a field of view of the infrared camera encompasses an inspection area on a surface of the composite structure;
    (b) activating at least one flash lamp to output light that illuminates at least portions of the inspection area;
    (c) activating the infrared camera to acquire infrared imaging data while the field of view of the infrared camera encompasses at least the inspection area;
    (d) processing the infrared imaging data to create a thermal signature; and
    (e) determining whether the thermal signature is similar within a specified threshold to any one of a multiplicity of reference thermal signatures stored in a reference database or not, the reference thermal signatures having one or more characteristics indicating the presence of wrinkles.

2. The method as recited in claim 1, wherein step (d) comprises calculating a first derivative of the infrared imaging data over time.

3. The method as recited in claim 1, wherein step (d) comprises calculating a second derivative of the infrared imaging data over time.

4. The method as recited in claim 1, further comprising accepting the composite structure if the thermal signature is not similar within the specified threshold to any one of the reference thermal signatures.

5. The method as recited in claim 1, further comprising:
    (f) measuring a wavelength of wrinkles using infrared imaging data that is indicative of the presence of wrinkles under the surface of the inspected area;
    (g) retrieving a transfer function from the reference database corresponding to a reference thermal signature that is similar within the specified threshold to the thermal signature created in step (d); and (h) applying the retrieved transfer function to the measured wavelength to estimate an actual wavelength of the wrinkles, wherein steps (f) through (h) are performed if the thermal signature is similar within the specified threshold to any one of the reference thermal signatures.

6. The method as recited in claim 5, further comprising:

(i) moving an ultrasonic transducer array to a location whereat 15 the ultrasonic transducer array overlies the inspection area on the surface of the composite structure;

(j) activating the ultrasonic transducer array to transmit ultrasound waves into the composite structure in the inspection area;

(k) acquiring ultrasonic imaging data representing ultrasonic echoes returned from the inspection area;

(l) estimating an actual amplitude of the wrinkles based on the ultrasonic imaging data;

(m) calculating a wrinkle wavelength-to-amplitude ratio using the estimated actual wavelength and estimated actual amplitude of the wrinkles; and (n) determining whether the wrinkle wavelength-to-amplitude ratio calculated in step (m) is outside an allowable range or not.

7. The method as recited in claim 6, further comprising accepting the composite structure if the wrinkle wavelength-to-amplitude ratio is not outside the allowable range.

8. The method as recited in claim 6, further comprising rejecting the composite structure if the wrinkle wavelength-to-amplitude ratio is outside the allowable range.

9. The method as recited in claim 6, further comprising inputting the wrinkle wavelength-to-amplitude ratio, along with orientation information, into a stress model to model the impact of the wrinkles on performance of the composite structure.

10. A method for inspecting a composite structure comprising:

(a) acquiring infrared imaging data from an inspected area on a surface of the composite structure using an infrared camera, said infrared imaging data being indicative of the presence of wrinkles under the surface of the inspected area;

(b) processing the infrared imaging data to estimate a value of a first wrinkle dimensional parameter of the wrinkles under the surface of the composite structure in the inspected area;

(c) subsequent to step (a), acquiring ultrasonic imaging data from the inspected area on the surface of the composite structure using an ultrasonic transducer array;

(d) processing the ultrasonic imaging data to estimate a value of a second wrinkle dimensional parameter of wrinkles under the surface of the composite structure in the inspected area;

(e) calculating a value of a wrinkle parameter which is a function of the first and second wrinkle dimensional parameters; and (f) determining a status of the composite structure in dependence on whether the value of the wrinkle parameter calculated in step (e) is inside or outside an allowable range of values.

11. The method as recited in claim 10, wherein step (c) comprises calculating a first derivative of the infrared imaging data over time.

12. The method as recited in claim 10, wherein step (c) comprises calculating a second derivative of the infrared imaging data over time.

13. The method as recited in claim 10, wherein the first wrinkle dimensional parameter is wrinkle wavelength.

14. The method as recited in claim 13, wherein the second wrinkle dimensional parameter is wrinkle amplitude.

15. The method as recited in claim 14, wherein the wrinkle parameter is a ratio of the wrinkle wavelength to the wrinkle amplitude.

16. The method as recited in claim 15, further comprising inputting the ratio of the wrinkle wavelength to the wrinkle amplitude deduced from infrared thermography time-temperature curves, along with orientation information, into a stress model to model the impact of the wrinkles on performance of the composite structure.

17. A method for measuring features in a composite structure made of a composite material and having a thickness, the method comprising:

(a) establishing a reference database containing transfer functions that relate true wrinkle wavelength to measured wrinkle wavelength in a multiplicity of reference standards made of the same composite material and having the same thickness as the composite structure to be inspected, the reference database further containing, for each transfer function, associated wrinkle dimensional data representing at least known depths, amplitudes and wavelengths of wrinkles in the multiplicity of reference standards;

(b) activating at least one flash lamp to output light that illuminates an area on a surface of the composite structure;

(c) activating an infrared camera to acquire infrared imaging data representing a temperature of the surface of the composite structure in at least a portion of the area illuminated in step (b);

(d) processing the infrared imaging data to identify the presence of wrinkles in a portion of the composite structure underneath at least a portion of the illuminated area;

(e) measuring a time required to get a maximum contrast between the wrinkled portion and a surrounding non-wrinkled portion of the composite structure;

(f) measuring a wavelength of wrinkles imaged by the infrared imaging data;

(g) estimating a depth of the wrinkled portion based on the time measured in step (e);

(h) using the estimated depth and the measured wavelength to retrieve a transfer function from the reference database; and (i) applying the retrieved transfer function to the measured wavelength to estimate an actual wavelength of the wrinkles in the wrinkled portion of the composite structure.

18. The method as recited in claim 17, wherein step (d) comprises calculating a first derivative of the infrared imaging data over time.

19. The method as recited in claim 17, wherein step (d) comprises calculating a second derivative of the infrared imaging data over time.

20. The method as recited in claim 17, further comprising:

(j) activating an ultrasonic transducer array to transmit ultrasound waves into the wrinkled portion of the composite structure;

(k) acquiring ultrasonic imaging data representing ultrasonic echoes returned from the portion of the composite structure;
(l) estimating an actual amplitude of the wrinkles based on the ultrasonic imaging data;
(m) calculating a wrinkle wavelength-to-amplitude ratio using the estimated actual wavelength and estimated actual amplitude of the wrinkles; and
(n) determining whether the wrinkle wavelength-to-amplitude ratio calculated in step (m) is outside an allowable range or not.

* * * * *

UNITED STATES PATENT AND TRADEMARK OFFICE
CERTIFICATE OF CORRECTION

PATENT NO. : 9,519,844 B1
APPLICATION NO. : 15/004119
DATED : December 13, 2016
INVENTOR(S) : Jeffrey G. Thompson et al.

Page 1 of 1

It is certified that error appears in the above-identified patent and that said Letters Patent is hereby corrected as shown below:

In the Specification

After the Title on Line 4 in Column 1, insert the following section:
--STATEMENT REGARDING FEDERALLY
SPONSORED RESEARCH OR DEVELOPMENT
This invention was made with Government support under Contract No. NN09AA00A awarded by the National Aeronautics and Space Administration. The Government has certain rights in this invention.--

Signed and Sealed this
Twenty-second Day of October, 2019

Andrei Iancu
*Director of the United States Patent and Trademark Office*